United States Patent [19]
Byra et al.

[11] Patent Number: 6,013,278
[45] Date of Patent: Jan. 11, 2000

[54] LIPOSOMAL ANTINEOPLASTON THERAPIES WITH MARKEDLY IMPROVED ANTINEOPLASTIC ACTIVITY

[75] Inventors: Anna Byra; Stanislaw R. Burzynski, both of Houston; Robert J. Waldbillig, The Woodlands, all of Tex.

[73] Assignee: Burzynski Research Institute, Houston, Tex.

[21] Appl. No.: 08/856,133

[22] Filed: May 14, 1997

Related U.S. Application Data

[60] Provisional application No. 60/017,616, May 14, 1996.

[51] Int. Cl.⁷ .................................................. A61K 9/127
[52] U.S. Cl. .......................... 424/450; 514/299; 514/557; 514/646
[58] Field of Search ........................... 424/450; 514/299, 514/557, 646

[56] References Cited

U.S. PATENT DOCUMENTS

| | | | |
|---|---|---|---|
| 4,470,970 | 9/1984 | Burzynski | 424/177 |
| 4,522,803 | 6/1985 | Lenk et al. | 424/1.1 |
| 4,522,811 | 6/1985 | Eppstein et al. | 514/2 |
| 4,621,055 | 11/1986 | Theuver | 435/69 |
| 4,663,167 | 5/1987 | Lopez-Berestein | 514/37 |

(List continued on next page.)

FOREIGN PATENT DOCUMENTS

| | | |
|---|---|---|
| 0 069 232 A2 | 1/1983 | European Pat. Off. . |
| 0 219 922 A3 | 4/1987 | European Pat. Off. . |
| 0 393 575 A1 | 10/1990 | European Pat. Off. . |
| WO89/06977 | 8/1989 | WIPO . |
| WO91/16309 | 8/1991 | WIPO . |
| WO92/04043 | 3/1992 | WIPO . |
| WO93/24123 | 12/1993 | WIPO . |

OTHER PUBLICATIONS

Ranade in J. Clin. Pharm. 29, pp. 685–694, 1989 (Drug delivery system).

Weiner in Drug dev. & Indust. Pharmacy. 15(10) pp. 1523–1554 (1989).

Xiang et al., "Development of a Combined NMR Paramagnetic Ion–Induced Line–Broadening/Dynamic Light Scattering Method for Permeability Measurements Across Lipid Bilayer Membranes, " *Journal of Pharmaceutical Sciences* 84: 1308–1315 (1995).

*Primary Examiner*—Gollamudi S. Kishore
*Attorney, Agent, or Firm*—Arnold, White & Durkee

[57] ABSTRACT

A second generation of antineoplaston therapies with markedly improved antineoplastic activity is disclosed. Among others, members of the antineoplaston family include phenylacetate (PN), 3-phenylacetyl-amino-2, 6, piperidinedione (CN), and hydrolysis derivatives of CN: phenylacetylglutamine (PG) and isophenylacetylglutamine (Iso-PG). In part, these increases in antineoplastic activity result from large increases in the transport of antineoplaston compositions into cells. Importantly and unexpectedly these increases in antineoplastic activity also result from the capacity of the drug delivery system to direct antineoplaston compounds intracellular trafficking to intracellular binding sites influencing cell viability and proliferation. Liposomal formulations of antineoplaston compositions increase in vitro antineoplastic activity by a factor of 750 to 1500 as compared to administration of antineoplaston compounds given without liposomal formulations. In addition, these liposomal formulations enhanced cellular uptake of antineoplaston compounds from 30 to more that 80 fold. Liposomal formulations were also found to increase intracellular levels of the antineoplaston CN (3-phenylacetyl-amino-2,6, piperidinedione) by directing CN to intracellular binding sites that influence cell viability and proliferation and block its hydrolysis. Under conditions where free CN has no antineoplastic activity, liposomally formulated CN can produce essentially complete and relatively long-lasting blockade of cell growth. Cell growth was found to be restored as intracellular levels of bound CN decrease to undetectable levels.

7 Claims, 15 Drawing Sheets

U.S. PATENT DOCUMENTS

| | | | |
|---|---|---|---|
| 4,766,046 | 8/1988 | Abra et al. | 424/450 |
| 4,971,802 | 11/1990 | Tarcsay et al. | 424/450 |
| 5,116,622 | 5/1992 | Burzynski | 424/545 |
| 5,194,266 | 3/1993 | Abra et al. | 424/450 |
| 5,238,947 | 8/1993 | Hendry | 514/328 |
| 5,288,499 | 2/1994 | Janoff et al. | 424/450 |
| 5,443,839 | 8/1995 | Meybeck | 424/450 |
| 5,811,119 | 9/1998 | Mehta | 424/450 |

LIPOSOMAL ANTINEOPLASTON THERAPIES WITH MARKEDLY IMPROVED ANTINEOPLASTIC ACTIVITY

The present application claims priority of Provisional Application Ser. No. 60/017,616 filed May 14, 1996. The entire text of the above-referenced disclosure is specifically incorporated by reference herein without disclaimer.

BACKGROUND OF THE INVENTION

1. Field of the Invention

The present invention relates to pharmaceutical compositions comprising antineoplaston agents.

2. Description of Related Art

The antineoplaston agents are a family of naturally occurring non-toxic compounds believed to play a role in health and disease by producing and maintaining cellular differentiation. Antineoplaston agents are currently synthesized chemically but were initially isolated and characterized as natural constituents of body fluids. Among others, members of the antineoplaston family include 3-phenylacetyl-amino-2,6, piperidinedione (CN) and hydrolysis derivatives of CN: phenylacetylglutamine (PG) and iso-phenylacetylglutamine (Iso-PG), and phenylacetate (PN).

The three major forms of antineoplaston therapy, designated AS2-1, A-10, and CN therapies, are currently being evaluated for antineoplastic efficacy in multicenter phase II clinical trials. AS2-1 contains an 8:1 molar ratio of PN and L-PG and can be administered either intravenously or orally. A-10 therapy contains 4:1 molar ratio of PG and Iso-PG and is administered intravenously. Each of the A-10 components is racemic and optically inactive. CN therapy is a monotherapy consisting of racemic (optically inactive) CN that is administered orally.

In vitro dose-response studies on the individual components of antineoplaston therapy demonstrate that, on a molar basis, CN has the most potent antineoplastic activity. A problematic feature of CN, however, is that its solubility limits the highest testable concentration to ~0.8 mM. At this concentration, CN produces only a 50% suppression of cell growth. The other, less potent, antineoplaston agents have higher solubility and this allows their intrinsically lower potency to be off-set by higher (e.g., 30 mM) concentrations. As a result of these higher concentrations, the less active antineoplaston agents (on a molar basis) produce a more complete suppression of cell growth. The uniquely non-toxic characteristics of the soluble antineoplastons allow plasma levels to be increased to a level well above that needed to suppress in vitro cell growth. However, with the less soluble antineoplastons such as CN, this strategy cannot be employed and alternative methods must be developed to increase CN solubility and cellular uptake.

SUMMARY OF THE INVENTION

The present invention provides pharmaceutical compositions comprising an antineoplaston agent in a liposomal formulation.

The pharmaceutical compositions provided by the present invention are antineoplaston therapies with markedly improved antineoplastic activity. In part, these increases in antineoplastic activity result from large increases in the rate of transport of antineoplaston agents into cells. Importantly and unexpectedly these increases in antineoplastic activity also result from the capacity of the drug delivery system to direct antineoplaston intracellular trafficking to intracellular binding sites influencing cell viability and proliferation.

The present invention provides liposomal formulations of antineoplaston agents 3-phenylacetyl-amino-2,6, piperidinedione (CN) and hydrolysis derivatives of CN: phenylacetylglutamine (PG) and iso-phenylacetylglutamine (Iso-PG), and phenylacetate (PN) that increase in vitro antineoplastic activity by a factor of 750 to 1500. In addition these liposomal formulations enhance cellular uptake of antineoplaston agents from 30 to more that 80 fold. The liposomal formulations of the present invention increase intracellular levels of the antineoplaston CN by directing CN to intracellular binding sites that block its hydrolysis and influence cell viability and proliferation. Under conditions where free CN has no antineoplastic activity, liposomally formulated CN can produce a complete and relatively long-lasting blockade of cell growth.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
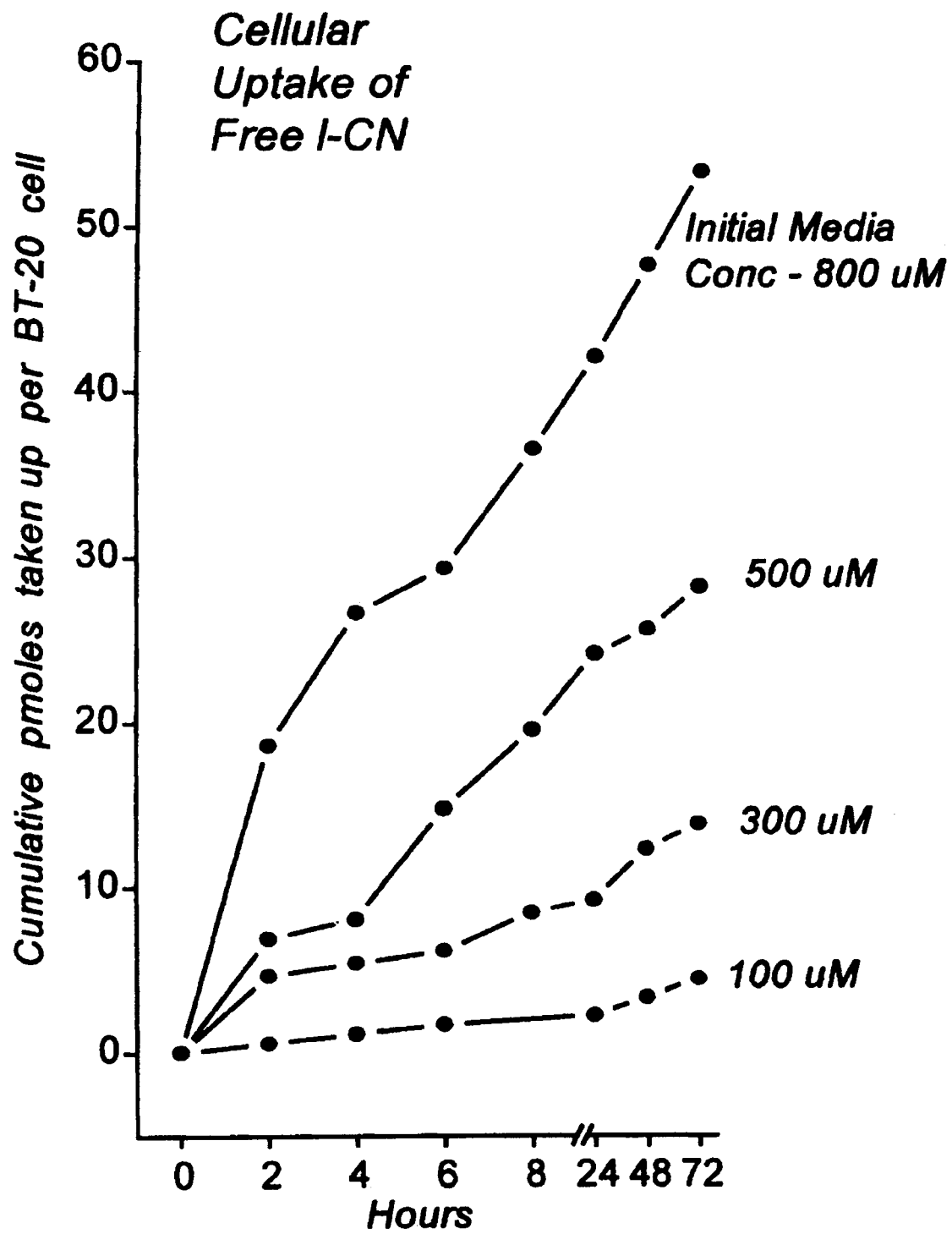
FIG. 1 shows the time course of the cellular uptake of free L-CN into BT-20 cells.

The present invention relates to pharmaceutical compositions comprising an antineoplaston agent in a liposomal formulation.

Antineoplastons are a family of naturally occurring nontoxic compounds believed to play a role in health and disease by producing and maintaining cellular differentiation. Among others, members of the antineoplaston family include
3-phenylacetyl-amino-2,6, piperidinedione (CN):

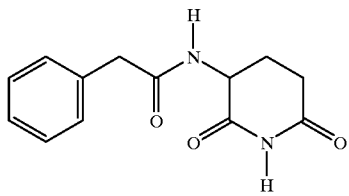

hydrolysis derivatives of CN, phenylacetylglutamine (PG):

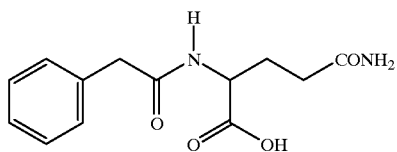

iso-phenylacetylglutamine (Iso-PG):

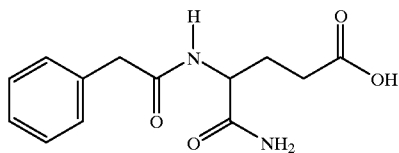

and phenylacetate (PN):

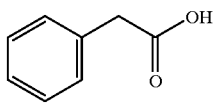

Also included as antineoplaston agents are their pharmaceutically acceptable salts. "Pharmaceutically acceptable salts" means salts having the biological activity of the parent compound and lacking unusually toxic activity at the selected administration level. Such salts include, but are not limited to, inorganic sodium, potassium and ammonium salts, organic diethanolamine, cyclohexylamine, and amino acid salts.

Liposomal formulations of the present invention can be made by any method known to those of skill in the art, such as those described by Bangham et al.(1965, *J. Mol. Biol.* 13: 238–252), Papahadjopoulos and Miller (1967, Biochim, Biophys. Acta. 135: 624–638), Science 267:1275 (1995), and those described in U.S. Pat. Nos. 5,288,499; 4,766,045; 4,224,179; and 4,235,871. A preferred method for liposome formation is to suspend a phospholipid in an organic solvent which is then evaporated to dryness leaving a deposit of phospholipid on the reaction vessel. An appropriate amount of aqueous phase is then added, the mixture is allowed to "swell", and the resulting liposomes which consist of multilamellar vesicles (hereinafter referred to as MLVs) are dispersed by mechanical means.

The antineoplaston agents of the present invention are added to the lipid composition prior to evaporation. The antineoplastons can be solubilized in a hot alcohol (e.g., methanol) and added to the lipid composition. The amount of active compound in the liposome will vary depending upon the lipophilic nature of the active compound(s), the components used to produce the liposome as well as the size and stability of the liposome. Generally, the molar ratio of antineoplaston to lipid will be between about 1:0.1 and 1:100, preferably between about 1:1 and 1:10. For PG the preferred ratio is about 1:3, and for CN the preferred ratio is about 1:1. The optimum size of the liposomes will vary depending upon the therapeutic target but the preferred size is between 0.1 and 100 micron. The preferred size is 0.1 to 0.5 microns.

Liposomes may be prepared from any surfactant or in combinations of surfactants but should be pharmaceutically acceptable. That is, the surfactants should not have or exhibit a deleterious effect on the host to which they are administered. Suitable surfactants are for example, ternary or complex lipids, glycerides, cerides, etholides and sterides, namely one of several compounds wherein the hydrophilic group is phosphate, carboxylate, sulfate, amino, hydroxyl or choline; and the lipophilic group is alkyl or alkylenyl, polyoxyalkylene or an alkyl group substituted with at least one aromatic or cycloalkyl group.

Preferred surfactants are phospholipid-related materials, such as lecithin, phosphatidyl ethanolamine, lysolecithin, lysophosphatidylethanolamine, phosphatidylserine, phosphatidyl inositol, sphingomyelin, cephalin, cardiolipin, phosphatidic acid, cerebrosides, dicetyl-phosphate, phosphatidylcholine and dipalmitoylphosphatidylcholine. Additionally, non-phosphorous-containing lipids are for example, stearylamine, dodecylamine, hexadecylamine, cetyl palmitate, glyceryl ricinoleate, hexadecyl stearate, isopropyl myristate, amphoteric acrylic polymers, triethanolamine-lauryl sulphate, alcoyl-aryl sulfonates, polyethyoxylated fatty acid amides and the like.

Various additives can be combined with the surfactant so as to modify its permeability characteristics or the superficial charge of the liposomes. Representative additives include long chain alcohols and diols; sterols, such as cholesterol; long chain amines and their quaternary ammonium derivatives; dihydroxyalkylamines; polyoxyethyleneated fatty amines; esters of long chain amino alcohols, their salts and quaternary ammonium derivatives; phophoric esters of fatty alcohols, such as sodium dicetyl phosphate; alkylsulfates, such as sodium cetyl sulfate; certain polymers such as polypeptides; carbohydrates; and proteins. The ratio of additive to lipid will vary with the additive (e.g. for cholesterol additive the weight ratio is generally between about 0.01 to 20, and is preferably between about 0.1 and 2; for carbohydrate additive the weight ratio is generally between about 0.01 to 1 and is preferably about 0.05 to 1).

The aqueous solution that is added to the evaporated lipid composition is generally a buffer solution, such as a buffered saline solution. The liposomes are then dispersed by mechanical means, such as shaking the solution with glass beads. The final size of the liposomes is produced by the process of filtration using filters with required pore diameters.

The active compound (e.g., CN, PG, PN, Iso-PG) either singly or in combination (e.g., A-10 containing appropriate molar ratios of PG : Iso-PG (e.g., 0.4: 1.0 to 40.0: 1.0; preferred ratio 4:1) or AS2-1 containing appropriate molar ratios of PN : PG) (e.g., 0.8:1 to 80.0:1 preferred 8:1) are included in a pharmaceutically acceptable carrier (preferred carrier=multilamellar or unilamellar, sterically stabilized liposomes, creams, oils and gels) in a diluent (preferred such as phosphate buffered or isotonic saline or gel oils or creams) in an amount sufficient to exert an inhibitory or therapeutic effect on diseases such as malignant melanoma or cancer of the brain, bone, breast, liver, prostate, ovary, cervix, panaceas, kidney, peripheral nervous, gastrointestinal tract, head, neck, adrenal gland, bladder, meninges, choroid plexus, soft tissue or Hodgkin's and non-Hodgkin's lymphoma, or viral disease (HIV), autoimmune disease, lymphocytic disease, neuroendocrine disease, profilerative disease of the skin in humans or animals, or disorders of the brain dopamine system such as Parkinson's Disease, Alzheimers, or schizophrenia.

The active materials can be administered by any appropriate route, for example, orally, parenterally, intracerebroventricular intrathecal intravenously, intradermally, subcutaneously intra-arterially, intraperitoneally; nasally, rectally, vaginally or topically. The intravenous route of administration is preferred.

The concentration of active compound(s) in the drug composition and its pattern of administration will depend upon absorption, inactivation, and excretion rates of the active compound and its carrier. Other factors known to others skilled in the art will also affect the concentration of the active compound(s). The drug composition may be administered once or divided into a number of smaller doses administered at varying intervals of time. Dose changes are understood to change depending upon the severity of the conditions, individual needs and professional judgment of the physician. Blood levels required to produce therapeutic effects are expected to be between 0.01 and 100 mM with the preferred blood level between 1 and 50 mM.

The results presented in the Examples below clearly show that liposomal formulations of antineoplastons can be used to greatly increase cellular uptake and antineoplastic activity.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of Liposomally Formulated Antineoplastons 3-phenylacetyl-amino-2, 6, piperidinedione (CN), phenylacetate (PN), phenylacetylglutamine (PG), antineoplaston A-10 (containing a 4:1 molar ratio of PG:Iso-phenylacetylglutamine (Iso-PG)) or antineoplaston AS2-1 (containing a 8:1 molar ratio of PN:PG) was solubilized in 5–10 ml of hot (55° C.) methanol (Mallincrodt) and added to a mixture containing a 1:1 molar ratio of egg L-lecithin and cholesterol (Sigma) dissolved in 5 ml of a 2:1 (v/v) mixture of methanol and chloroform (Aldrich). Because previous optimization studies determined that a test agent:lipid molar ratio of 1:3 maximizes compound entrapment and minimizes the formation of empty liposomes, this ratio was used in these Examples. Earlier work using human neuroblastoma (SK-N-MC) and human glioblastoma cells (U-18-MG) to examine the antineoplastic effect of liposomal A-10 was conducted with liposomes produced using a drug:lipid ratio of 1:30.

The test agent-lecithin-cholesterol mixture was evaporated to dryness in a 250 ml round bottom rotor evaporator (100 mM hg; 40–45° C.; 2 hr) and aqueous multilamellar liposomal vesicles were prepared by adding 20 ml of a phosphate buffered saline (PBS) and gently shaking with glass beads. The levels of liposomally entrapped compound were determined by rupturing the liposomes with chloroform, evaporating the chloroform and resuspending the test agent in dimethylforamide (DMF). The level of test agent escaping liposomal entrapment was determined by washing the liposomal preparation three times in PBS (centrifugation 15 k×g; 20 min; 4° C.) and analyzing the wash with a standardized and validated HPLC method (C-18 columns and a methanol:HOH:acetic acid (25:75:1 (v/v)) solvent system).

The time-course and concentration dependency of the cellular uptake of free and liposomally formulated antineoplaston agents in Examples 2, 3 and 4 were assayed by monitoring reductions in media concentrations. The uptake of these antineoplaston agents were examined in BT-20 human breast cancer cells.

EXAMPLE 2

Cellular Uptake of Free and Liposomal D- and L-CN

Cellular uptake of free D- and free L-CN (3-phenylacetyl-amino-2, 6, piperidinedione) were investigated in BT-20 cells. Cells were plated in 200 $\mu$l of media (3,000 cells/well—96 well plates), and 24 or 96 hrs later the plating media was replaced with fresh media containing free CN at final concentrations of 100, 300, 500, 800 $\mu$M. The levels of CN remaining in the media were determined following 0, 2, 4, 6, 8, 24, 48 and 72 hours of incubation. When the cellular uptake of liposomal antineoplastons was assessed, the total levels of liposomes were equivalent across all levels of the test agents. Unilaminar liposomal vesicles containing antineoplaston agents were prepared within 24 hours of an experiment by passing multilamellar vesicles through a 0.2 micron filter several times. The unilaminar vesicles were then added to the media at the appropriate concentration and sterilized using a 0.2 micron filter.

At the indicated times after the addition of the test compound, the media was harvested, centrifuged (110 ×g; 10 min; 4° C.) and the supernatant stored at −70° C. until assayed using a validated HPLC method. For each test agent, all concentrations were tested at all time points and there were six replicate wells at each time point. Media from the replicate wells was pooled for the HPLC analysis. Compound levels were determined with at least two HPLC injections and the variance between injections was less than 10%.

To verify that the reductions in media test agent concentrations were related to cellular uptake (and not to degradation of the test agent by enzymes secreted by cells) the test agents were incubated in. BT-20 cell-conditioned media for 24 hrs (37° C.). It was found that at the end of such an incubation, test agents are recovered entirely as intact compound. The conditioned media for these experiments were obtained as an aliquot from 20 ml of media that had been conditioned for three days by 1×10$^6$ BT-20 cells.

Figure 2:
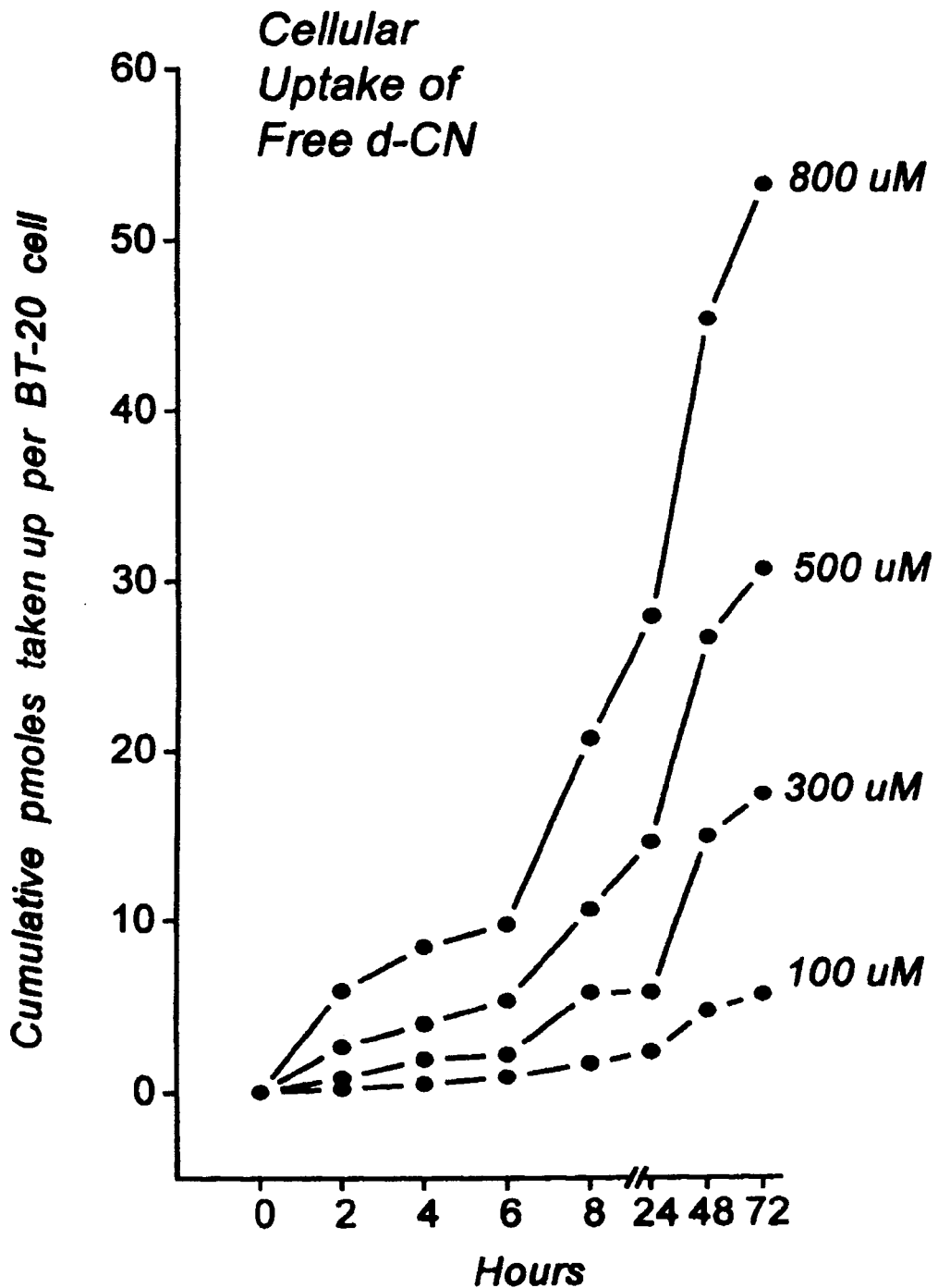
FIG. 2 shows the time course of the cellular uptake of free D-CN into BT-20 cells.

FIGS. 1 and 2 show that D- and L-CN are rapidly and extensively taken up by BT-20 cells. By comparing FIG. I to FIG. 2, it can be seen that, during the first six hours of the incubation, cells take up free L-CN more effectively than free D-CN. However, by 72 hours the uptake of the two CN isomers is approximately equivalent. It can be also seen in FIG. 1 that the uptake of CN is related to its concentration in the media.

FIG. 1 also shows that although BT-20 cells continue to take up L-CN for several days, the rate of uptake is diminished on the second and third days of the incubation. The degree of this slowing is concentration dependent with the cells exposed to the higher concentrations showing the largest reductions on day two. FIG. 2 shows that cells incubated with free D-CN do not exhibit this late stage reduction in CN uptake. Instead, uptake on the second day of incubation increases relative to that observed on the first day.

EXAMPLE 3

Cellular Uptake of Free PN

Cellular uptake of free PN was investigated in BT-20 cells. Cells were plated and samples prepared as in Example 2.

Figure 3:
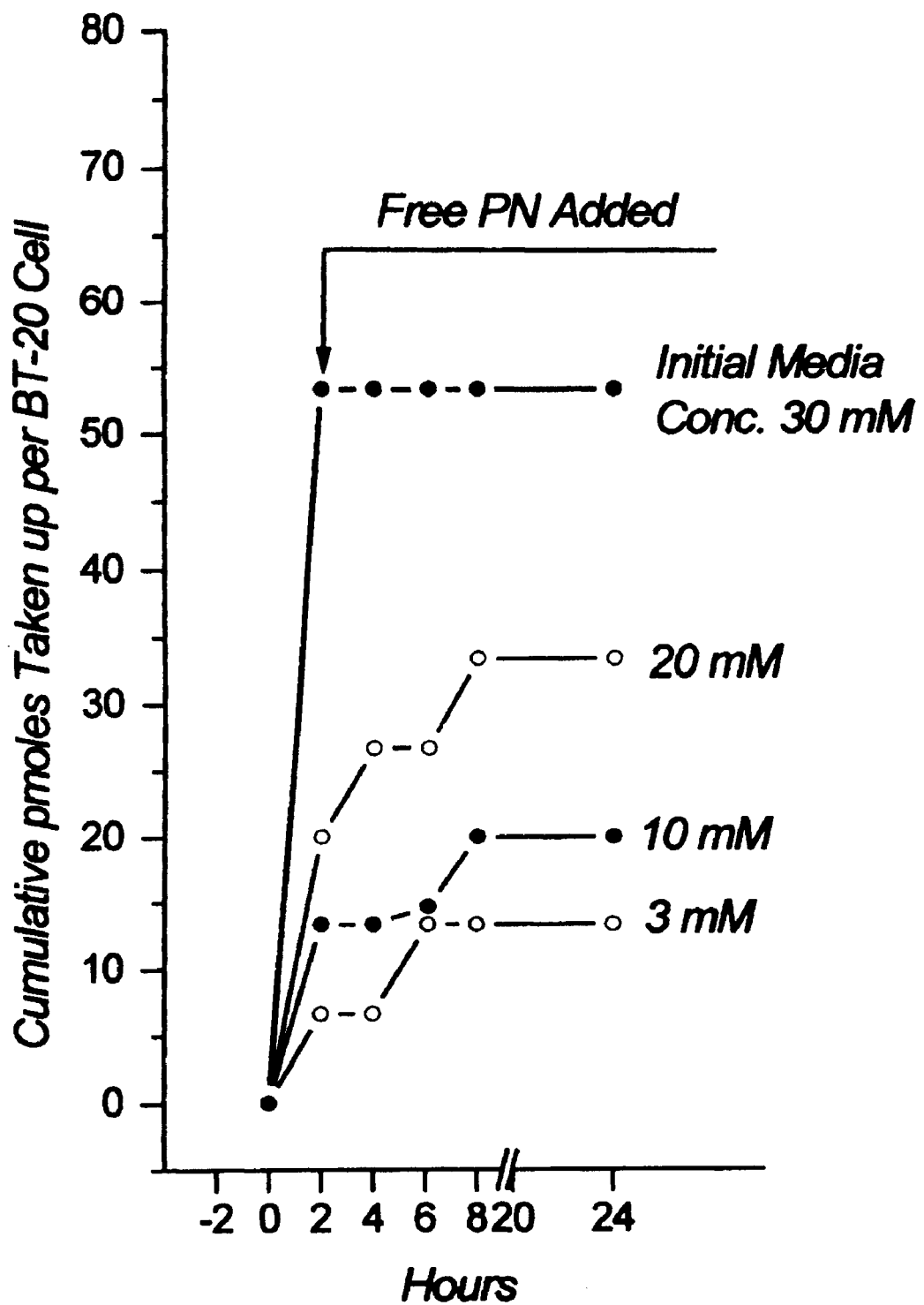
FIG. 3 shows the time course of the cellular uptake of free PN into BT-20 cells.
Figure 4:
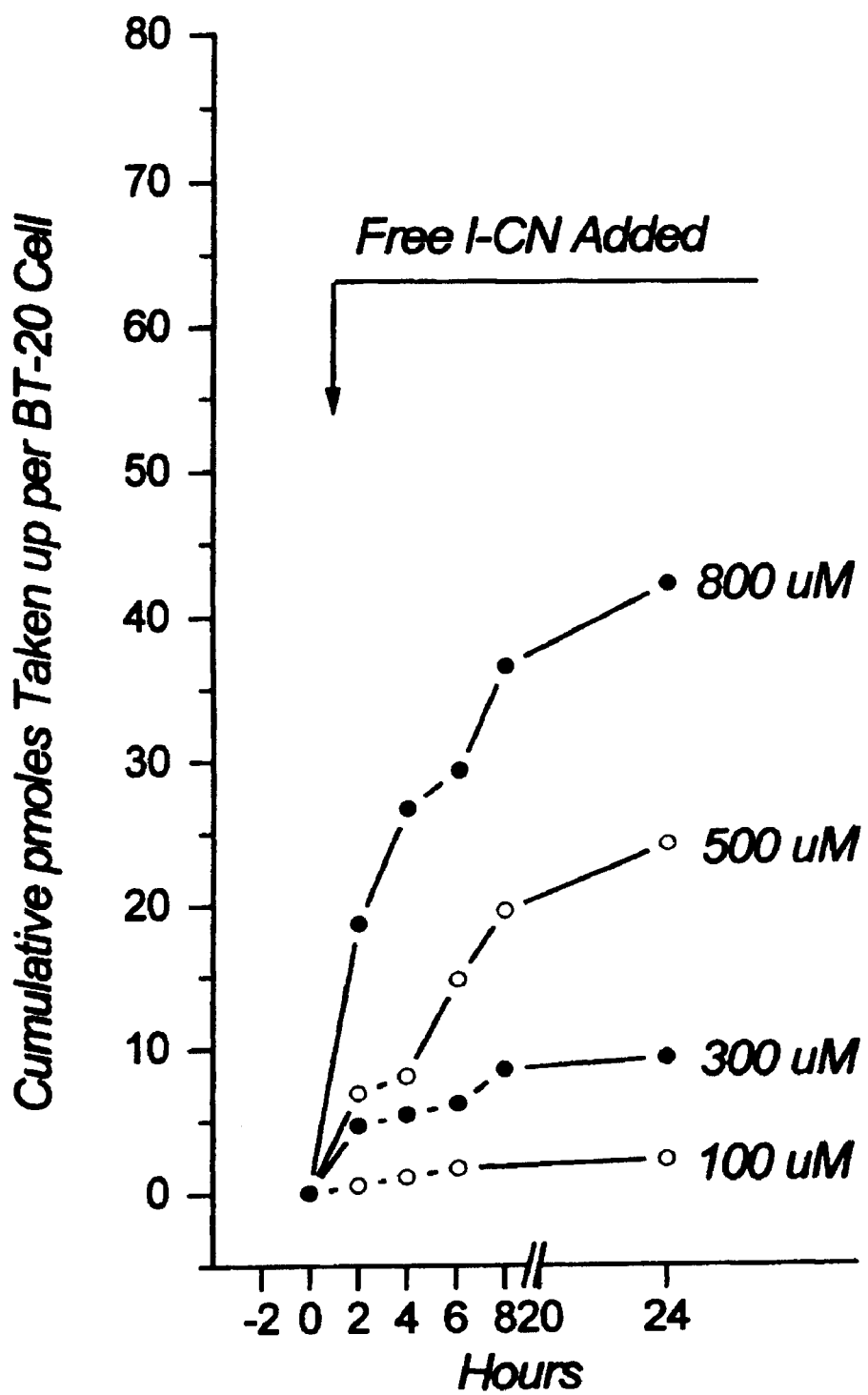
FIG. 4 shows the time course of the cellular uptake of free L-CN into BT-20 cells.

FIG. 3 shows the time course of free PN uptake by BT-20 cells. For purposes of comparison, FIG. 4 shows the uptake of L-CN. It can be seen that BT-20 cells exhibit a concentration- and time-dependent take up of PN. The dose-dependency results in an uptake of ~54 pmoles/BT-20 cell when the initial media concentration is 30 mM. In contrast, a 3.0 mM media concentration results in a transport of ~14 pmoles/BT-20 cell. The process mediating the cellular up take of PN exhibits dose dependency that interacts with time. That is, at high concentrations (e.g., 30 mM) uptake is completed within the first two hours. At lower concentrations the uptake process continues to function over a longer interval.

Figure 5:
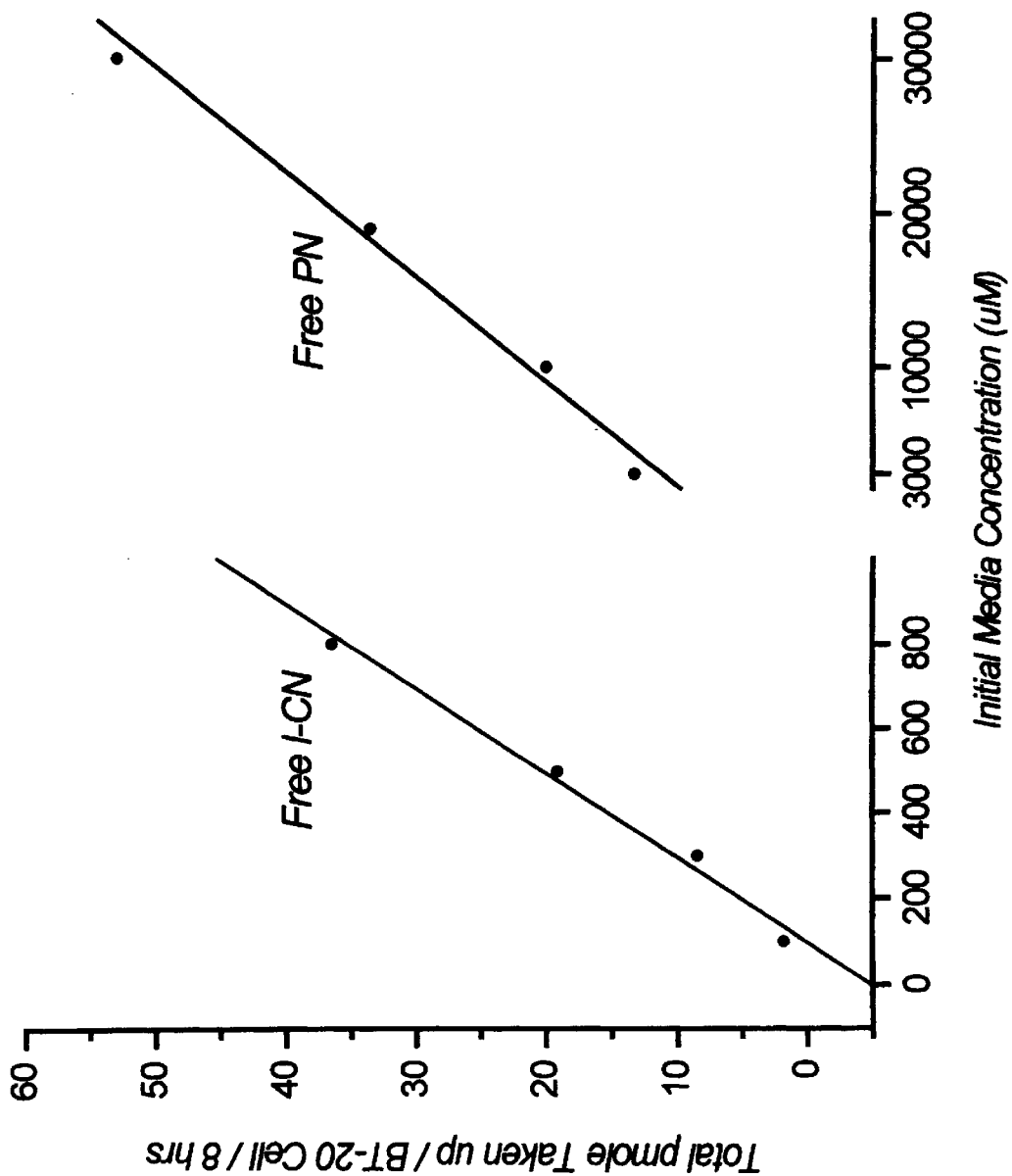
FIG. 5 shows the concentration dependence of the cellular uptake of free L-CN and PN into BT-20 cells.

A comparison of the uptake of free CN and PN is shown in FIGS. 3, 4 and 5. It can be seen in FIGS. 3 and 4 that the uptake of both compounds are time and dose dependent. FIG. 5 exemplifies the differential dose-dependency of free PN and CN uptake by BT-20 cells. It can be seen from this figure that by the end of an eight hour incubation, both compounds exhibit cellular uptake that is linearly related to media concentration. However, the concentration required to observe equivalent cellular uptake of these two compounds is very different. With PN, for example, uptake is seen at relatively high media concentrations (e.g., between 3 and 30 mM). In contrast, media concentrations between 0.1 and 0.8 mM are sufficient to observe CN uptake. It seems likely that these differences can be related to differences in the lipophilicity of the two compounds.

Although the uptake of free PN requires substantially higher concentrations for uptake to be observed, it should be pointed out that sufficient elevations of media concentration can produce levels of PN uptake very similar to those observed with CN. It is also interesting to point out that, for these two compounds, equivalent levels of antineoplastic activity (e.g., CN and PN $IC_{50}$~0.8 and 15 mM, respectively) are associated with approximately equivalent levels of uptake (e.g., ~30 pmoles/cell).

EXAMPLE 4

Cellular Uptake of Liposomal CN

Cellular uptake of liposomal CN was investigated in BT-20 cells. Cells were plated as in Example 2, and media containing 800 μM racemic (optically inactive), liposomally formulated CN was used to prepare the samples.

Figure 6:
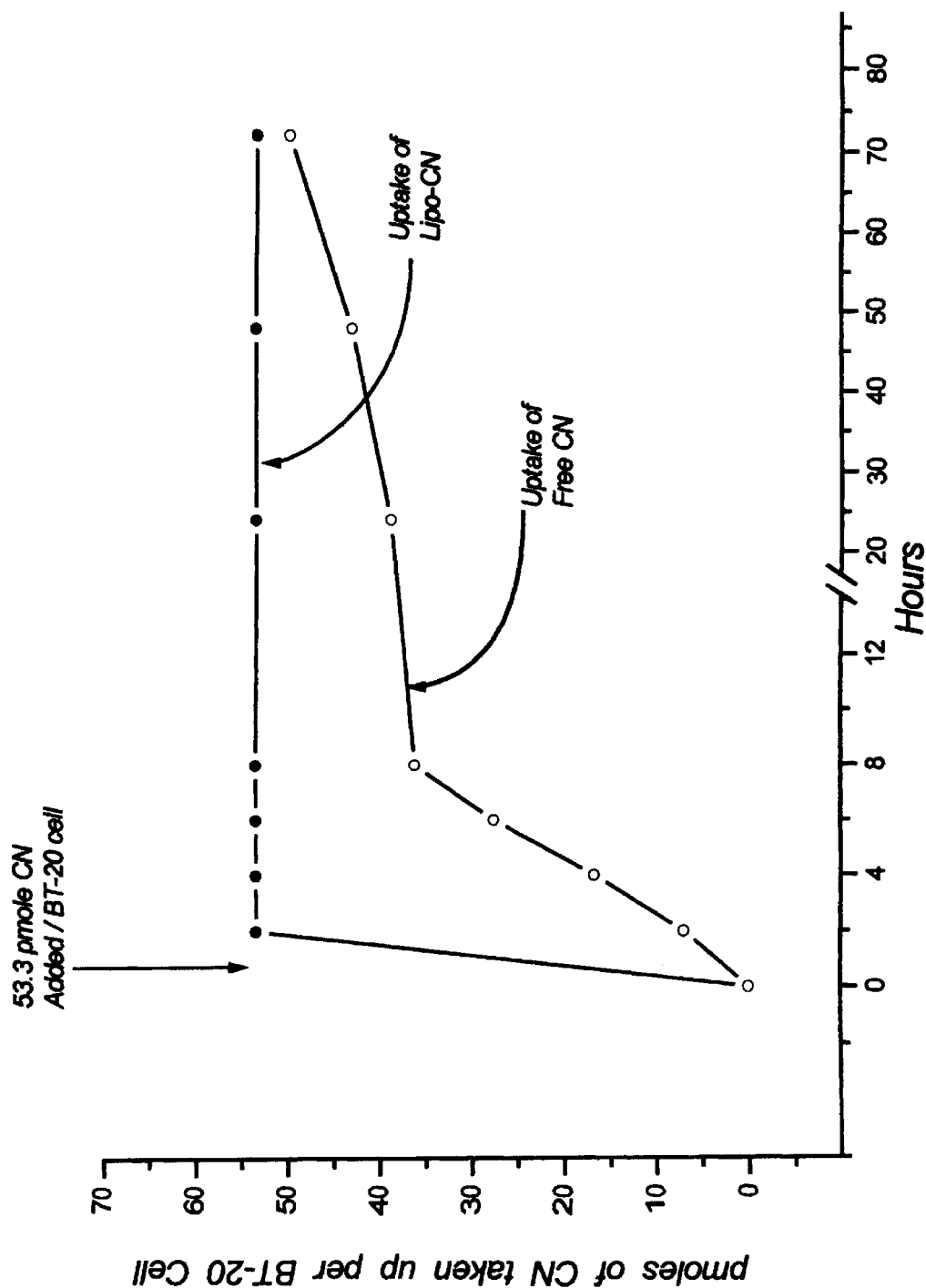
FIG. 6 shows the time course of the cellular uptake of free and liposomal CN into BT-20 cells.

Although free CN is taken up by BT-20 cells, liposomal formulations of CN markedly enhance this process. FIG. 6 shows the results of an experiment where free or liposomally formulated CN was added to six replicate cells each containing 3,000 BT-20 cells. It can be seen from this figure that within two hours of its addition liposomal CN is completely taken up by BT-20 cells. At the two hour time point, the uptake of liposomal CN is ten times greater than of free CN. The depletion of media liposomal CN levels during the first two hours of the incubation obviously prevents further uptake during the remaining 70 hours of the incubation. The uptake of free CN proceeds at a slower pace and, by the end of the 72 hour incubation period, its uptake finally achieves a level approximating that produced by liposomal CN during a two hour incubation.

EXAMPLE 5

Intracellular Metabolism of Free and Liposomal CN

The intracellular fate of free and liposomal CN was examined in BT-20 human breast cancer cells incubated with 800 μM racemic (optically inactive) CN (53 pmole/cell). At selected times the cells were washed (3×with PBS), trypsinized, pooled, and homogenized in 200 μl of isotonic saline. Following centrifugation (110×g; 15 min; 4° C.) the cell pellet and supernatant were separated for analysis using a validated HPLC method that, in addition to detecting CN, quantitatively determined the levels of PG and Iso-PG. In this study, data from HPLC peaks representing PG and Iso-PG were pooled and referred to as PG/Iso-PG. Antineoplaston components or their derivatives found in the supernatant are considered to be unbound or "free", while antineoplaston agents in the pellet are thought to be "bound" to protein or cellular structures easily pelleted by low gravity centrifugation.

Table 1 shows that during a 24 hr incubation both free and liposomal CN are extensively taken up by BT-20 cells. In the case of free CN by the end of a 24 hr incubation 43.2 pmoles (of the 53 pmoles added per cell) has been removed from the media. Despite this level of uptake intact CN cannot be found inside the cells. Instead it was found that the cells contained 36.7 pmoles of free intracellular PG/Iso-PG per cell. Since PG and Iso-PG are known to be the hydrolysis products of CN and these compounds cannot be detected in untreated cells it appears that intracellular hydrolysis of the CN taken up by cells produces relatively long-lived intracellular PG/Iso-PG.

TABLE 1

Uptake and Intracellular Levels of Free and Bound CN and PG/Iso-PG.

| Type of CN added | Compound | Uptake (pmole/cell) | Free Intracellular (pmole/cell) | Bound Intracellular (pmole/cell) |
|---|---|---|---|---|
| Non-Liposomal | CN | 43.2 | ND* | ND |
| Non-Liposomal | PG/Iso-PG | ND | 36.7 | ND |
| Liposomal | CN | 53.3 | ND | 4.3 |
| Liposomal | PG/Iso-PG | ND | 37.3 | 11.2 |

*Not detected

Formulating CN in liposomes markedly alters its intracellular fate. Table 1 shows that by the end of the incubation interval all of liposomal CN added to the media is taken up by cells. Of the 53 pmoles taken into the cells 70.0 percent (37.3 pmoles/cell) is found inside the cells as free PG/Iso-PG. Another 21.0 percent of the CN (1 1.2 pmoles/cell) is found as intracellular bound PG/Iso-PG. The remaining 8.1 percent of the liposomal CN taken up is found intracellularly as bound intracellular CN.

Figure 9:
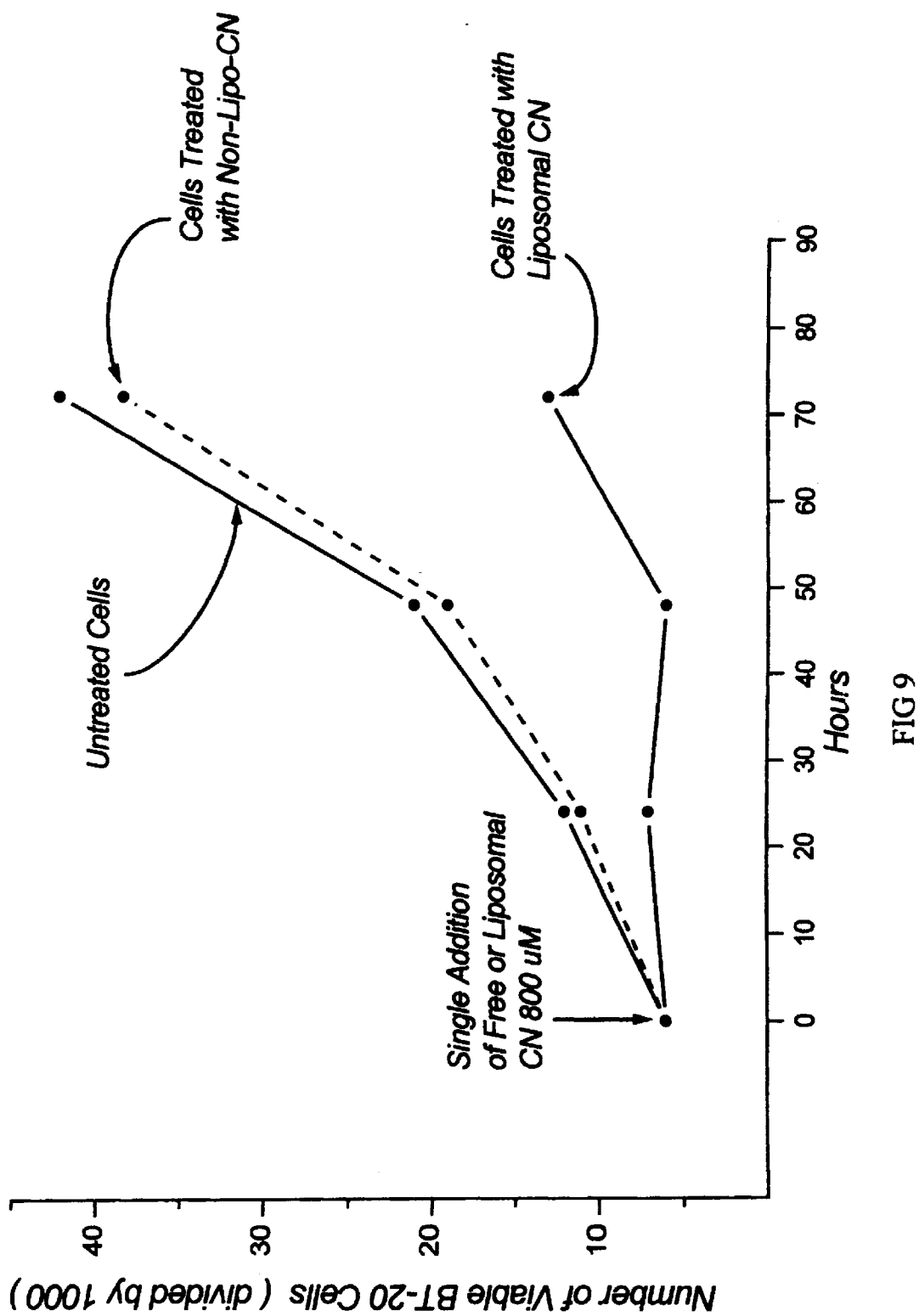
FIG. 9 shows the time course of BT-20 cell number after no treatment or treatment with liposomal or non-liposomal CN.

The observation that free and liposomal CN produce the same level of free intracellular PG/Iso-PG (36.7 and 37.3 pmole/cell, respectively) but different levels of bound CN and PG/Iso-PG is important since, in these conditions, only the liposomal CN exhibits antineoplastic activity (see FIG. 9). This suggests that that bound CN and/or PG, and not of free PG/Iso-PG, are causally related to the suppression of cell growth.

EXAMPLE 6

Time Course of Intracellular Metabolism of Liposomal CN

The data presented in Example 5 indicates that liposomal formulations alter the intracellular fate of CN. To better understand the time course of the intracellular fate of liposomal CN, BT-20 cells were exposed as in Example 5 to liposomal CN for 1, 2 and 4 hours. At each of these time points, cells were harvested and the intracellular levels of free and bound CN or PG/Iso-PG determined using the methods described in Example 5.

Figure 7:
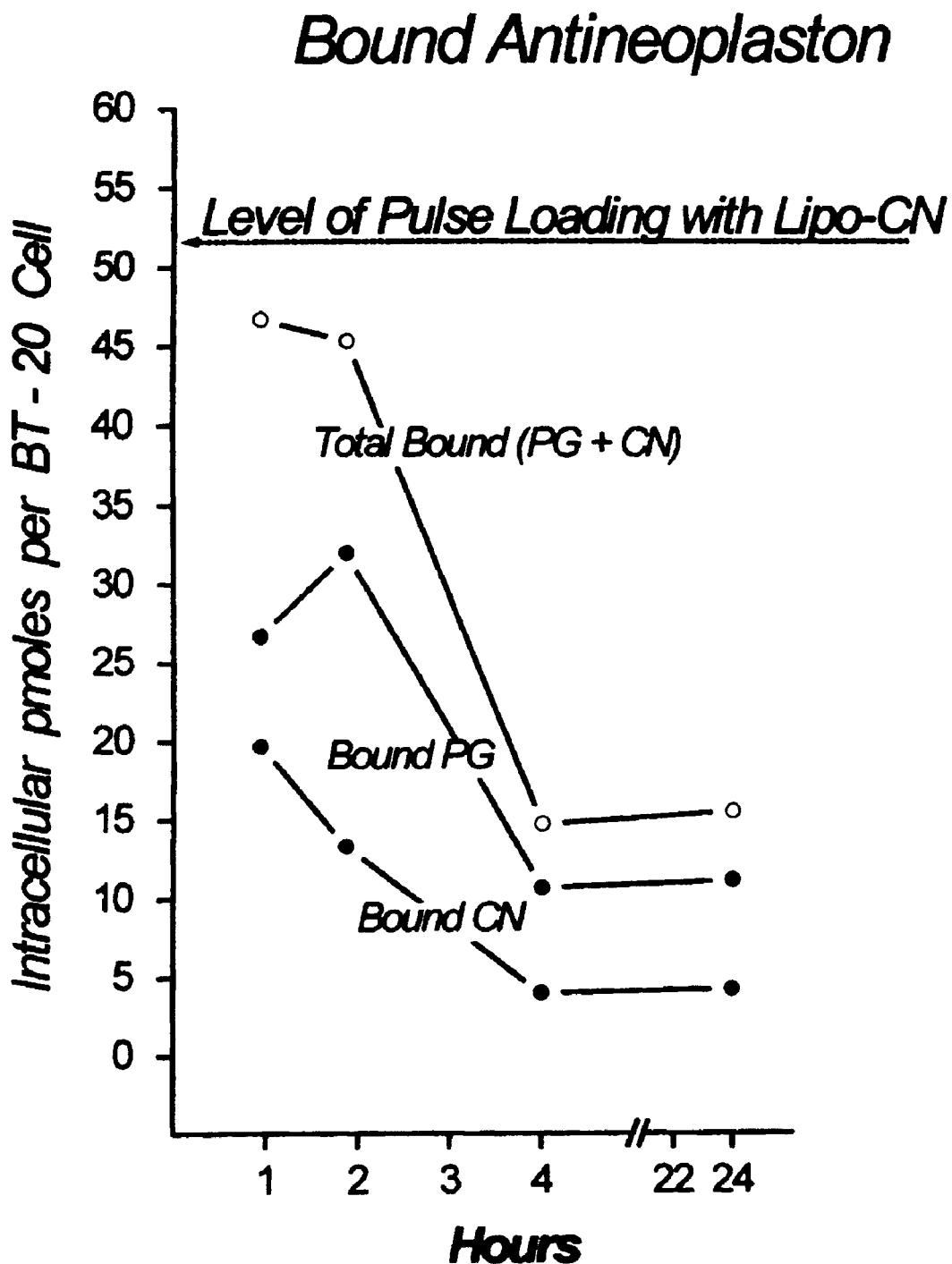
FIG. 7 shows the time course of bound antineoplastons in BT-20 cells.
Figure 8:
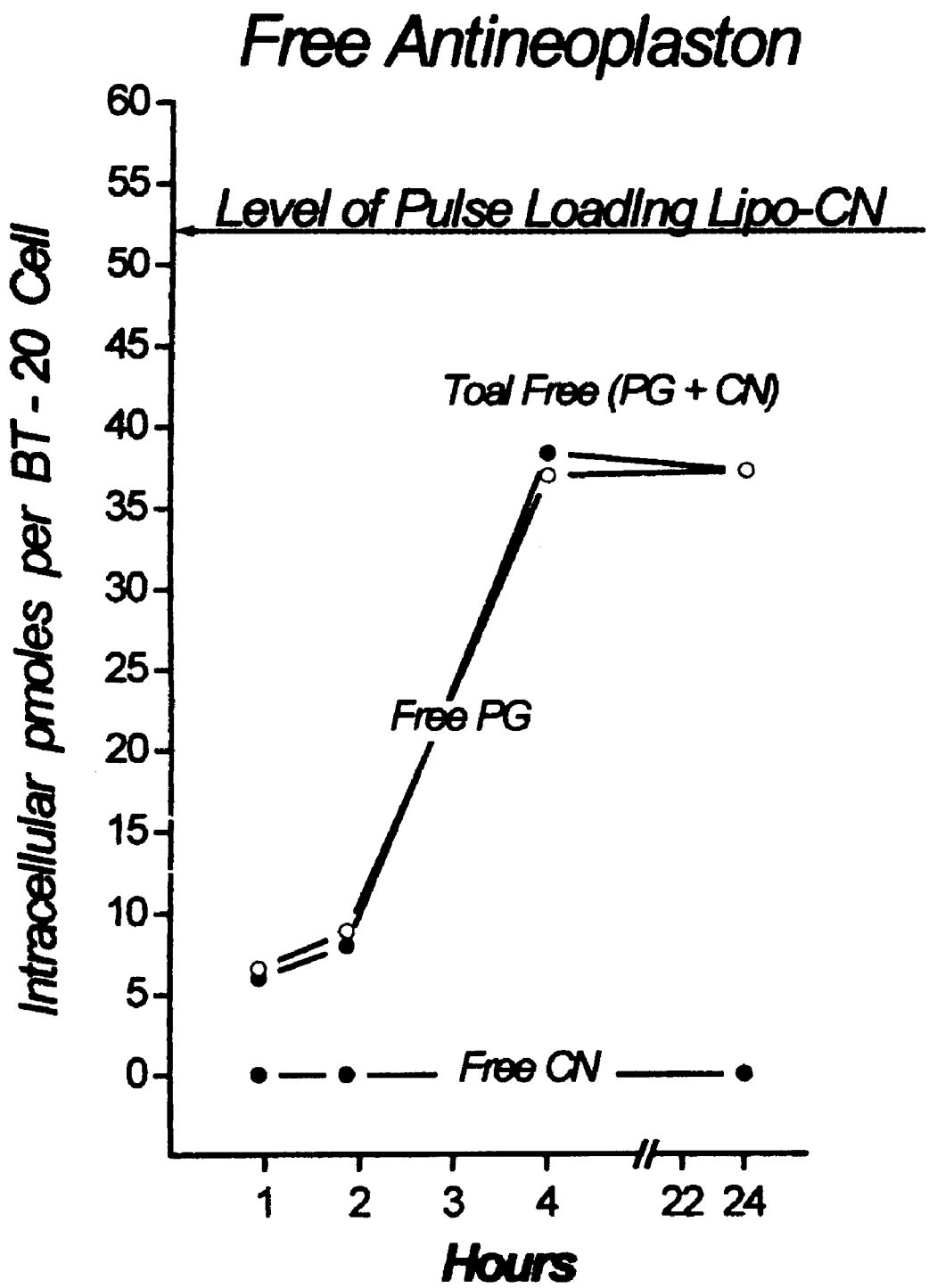
FIG. 8 shows the time course of free antineoplastons in BT-20 cells.

During the first hour of incubation all 52.4 pmoles of liposomal CN added per cell are taken up. Because of this it is clear that after this time point CN input to the cell has ceased. FIGS. 7 and 8 show that of the 52.4 pmoles of liposomal CN taken up per cell 37.0 percent is initially found intracellularly as bound CN, 51.0 percent as bound PG/Iso-PG. The remaining 8.0 percent of the liposomal CN taken up is found as free PG/Iso-PG.

FIGS. 7 and 8 show that during the second hour of the incubation, there is a slight decrease in the levels of bound CN (from 19.7 to 13.3 pmole/cell) and a concomitant increase in the bound and free forms of its hydrolysis products, PG/Iso-PG (i.e., bound PG/Iso-PG from 26.7 to 32.0 pmole/cell; free PG/Iso-PG from 6.0 to 8.0 pmoles/cell). Between the second and fourth hour of incubation, levels of bound CN and PG/Iso-PG decrease to 30.0 percent of their highest intracellular value. This decrease in bound CN and PG/Iso-PG is accompanied by a matching increase in free PG/Iso-PG. The levels of bound PG/Iso-PG and CN present at the end of the fourth hour remain level until the 24 hour time point.

EXAMPLE 7

Antineoplastic Activity of Free and Liposomal CN

The previous Examples demonstrated that liposomal formulations of CN increase intracellular levels of bound CN and PG/Iso-PG. To determine whether this effect leads to enhanced antineoplastic activity, the antineoplastic activity of free and liposomal CN was examined in BT-20 cells. These cells were plated at 3,000 cells per well (96 well plate) and one day later the plating media replaced with fresh media with or without free or liposomal CN (800 uM). Control cells in the liposomal condition received the equivalent levels of liposomes without CN. Following a 24, 48 or 72 hr incubation, cells from six replicate wells were pooled and the number of viable cells determined using trypan blue and a hemocytometer.

FIG. 9 shows that, relative to untreated cells, a single administration of free CN is ineffective in suppressing BT-20 cell growth. In contrast, the same concentration of liposomal CN completely blocked BT-20 cell proliferation. This suppression of cell growth is observed within 24 hrs of the addition of liposomal CN, remains strong at 48 hours, and appears to weaken after 72 hours.

The Examples above also demonstrate that liposomal formulations enhanced cellular uptake of CN, led to relatively long-lived increases in intracellular levels of bound CN and PG/Iso-PG and increased antineoplastic activity. The cells in this Example were therefore also analyzed for intracellular levels of CN and PG/Iso-PG to determine any correlation between the clearance of intracellular bound CN and/or ?G/Iso-PG and the resumption of cell growth.

Figure 10:
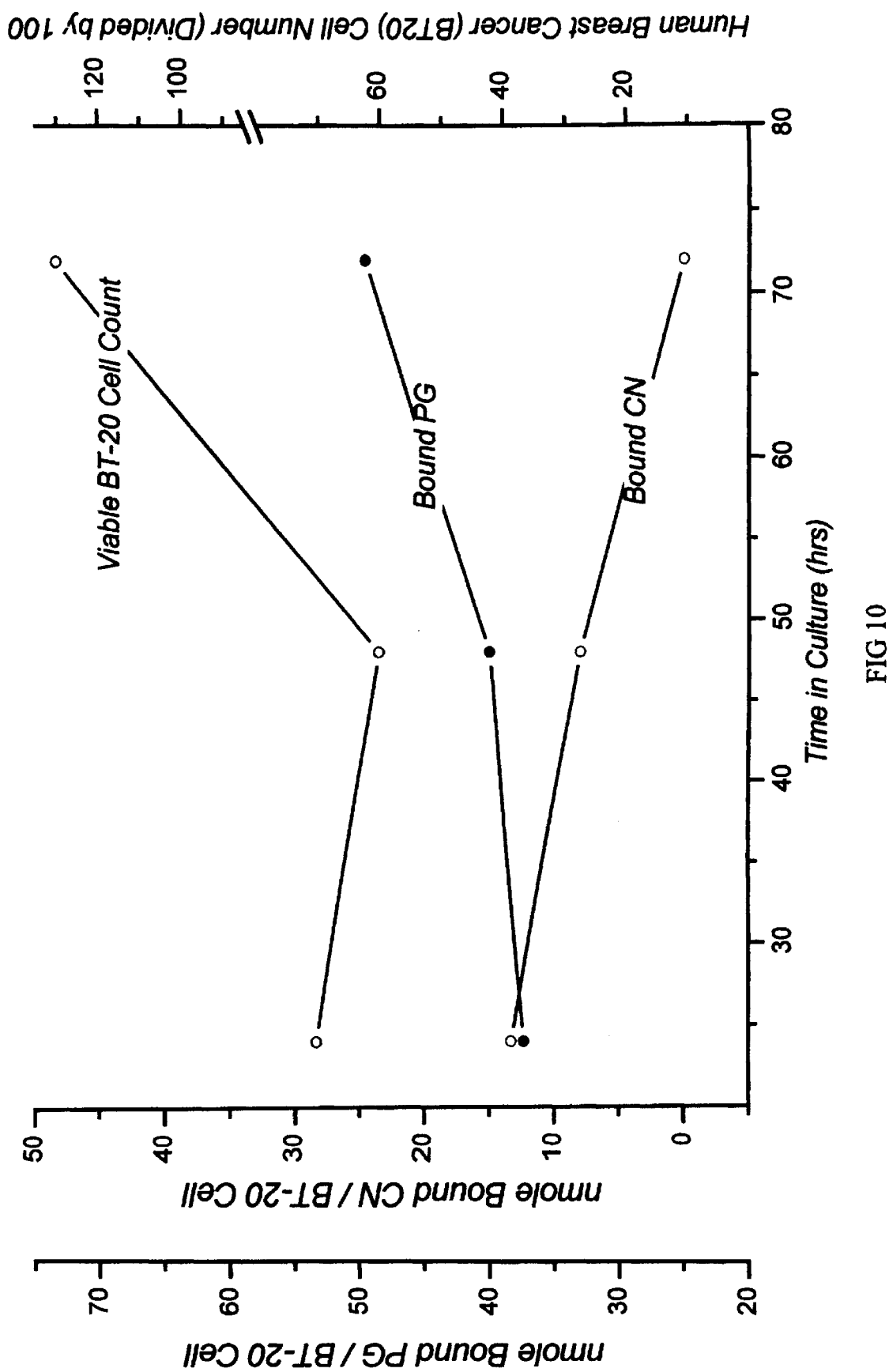
FIG. 10 shows the time course of intracellularly bound PG, bound CN and BT-20 cell number following treatment with liposomal CN.

FIG. 10 shows that levels of intracellular bound CN and PG/Iso-PG remain stable between 24 and 48 hrs after the initial dosing with liposomal CN. During this interval the BT-20 cell growth remains suppressed. Between 48 and 72 hrs the levels of bound CN decrease below detectable limits while levels of bound PG increase slightly. Correlated with the reduction in bound CN is the loss of the inhibition of BT-20 cell growth.

EXAMPLE 8

Antineoplastic Effects Free and Liposomal A-10

The effect of liposomal formulations on the antineoplastic activity of A-10 was examined in neuroblastoma (SK-N-MC) and glioblastoma (U-118-MG) cells. These cells were plated at 5000 cells/well (Falcon; 96 well plate). Twenty four hours following plating, the media was replaced with fresh media with or without various concentrations of free or liposomal A-10, or empty liposomes. Cells were exposed to the test agents for five days with a media change on day three. Neuroblastoma cells were maintained at 37° C. (5% $CO_2$) in Eagle's MEM with non-essential amino acids, sodium pyruvate and Earle's BBS with 10% fetal bovine serum. Glioblastoma cells were maintained at 37° C (5% $CO_2$) in Dulbecco's modified Eagle's medium, with 10% fetal bovine serum.

Figure 11:
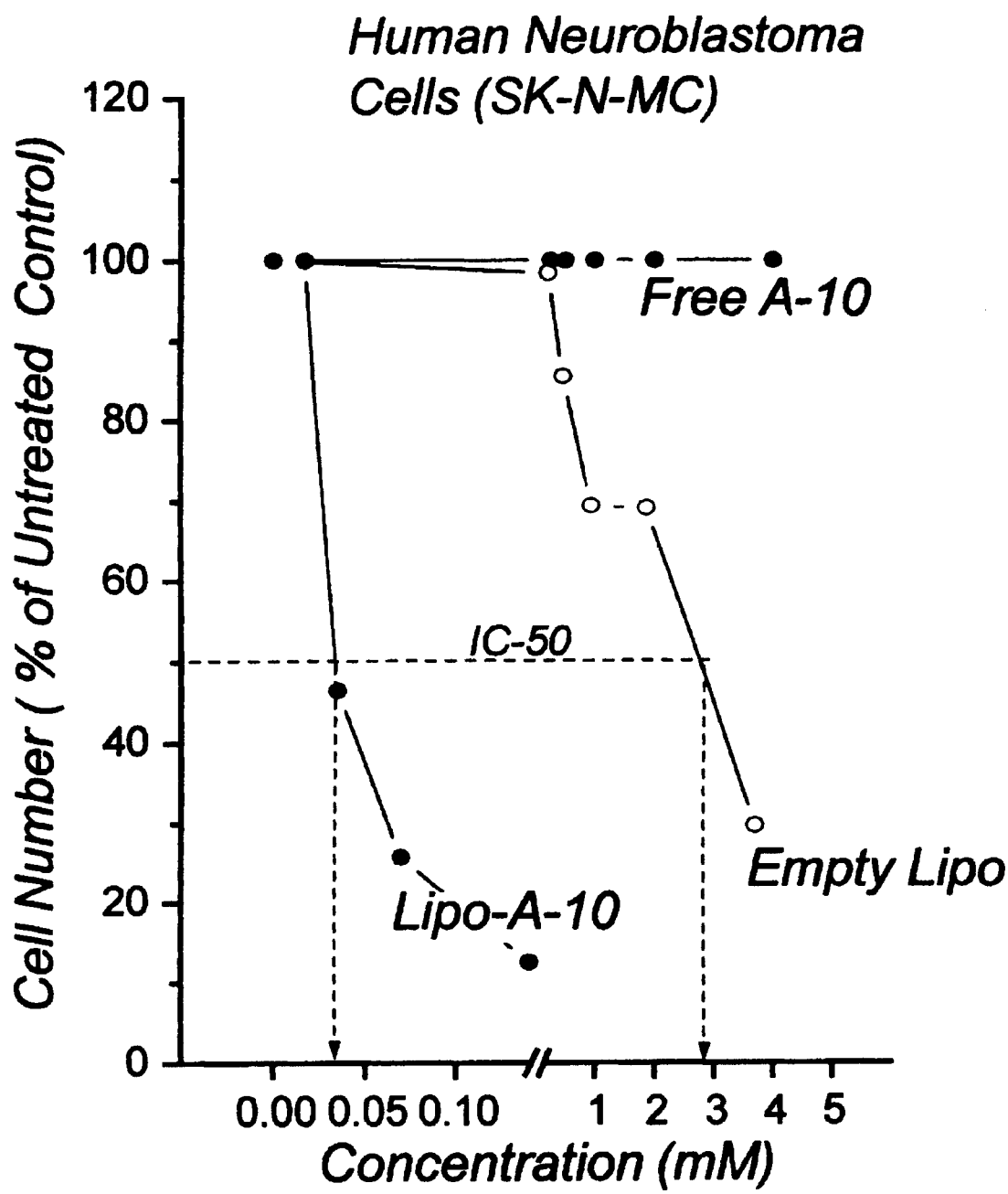
FIG. 11 shows the concentration dependence of cell numbers of human neuroblastoma cells following treatment with free A-10, liposomal A-10 or empty liposomes.
Figure 12:
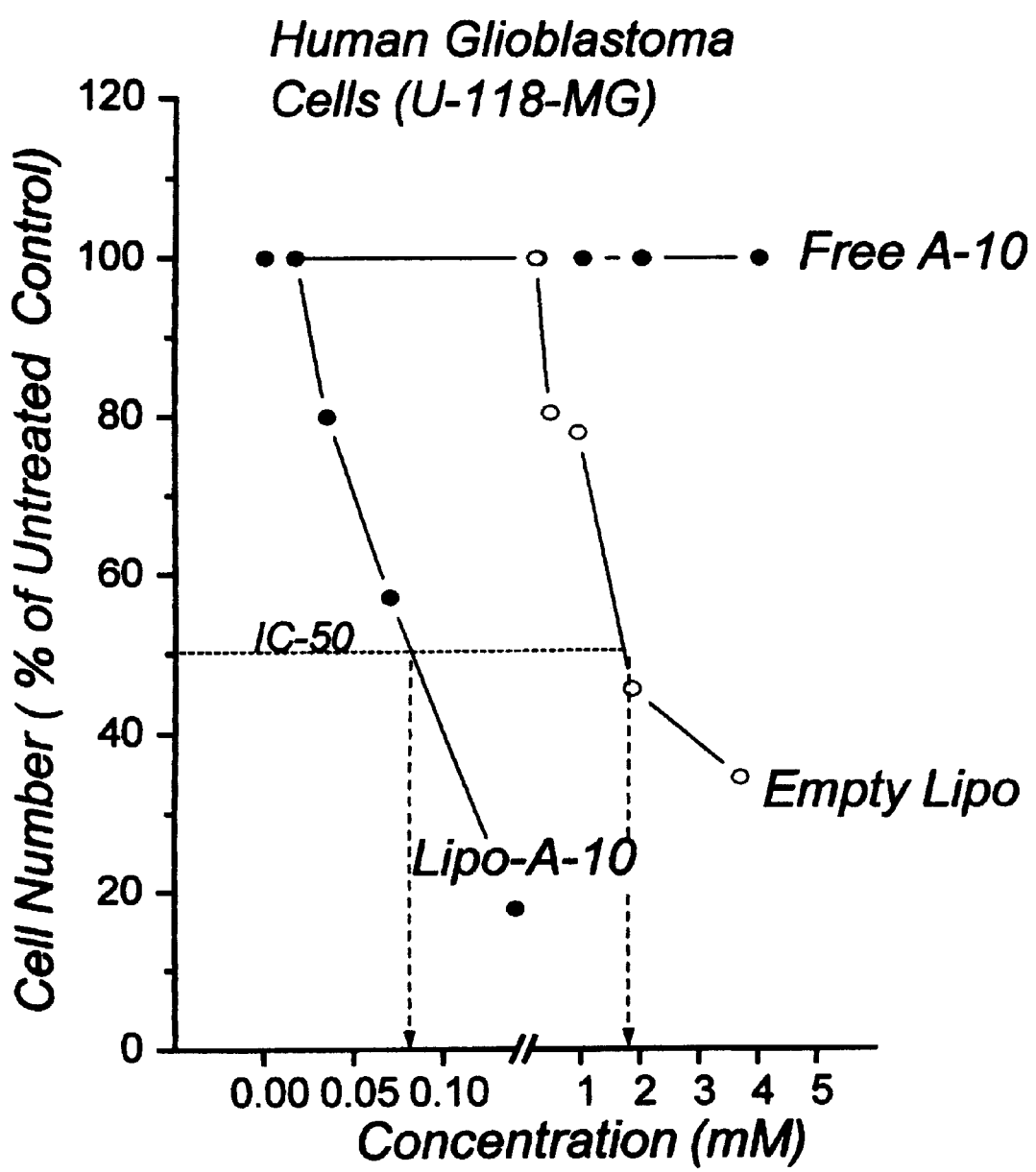
FIG. 12 shows the concentration dependence of cell numbers of human glioblastoma cells following treatment with free A-10, liposomal A-10 or empty liposomes.

It can be seen from FIGS. 11 and 12 that, at the concentrations employed in this study, free A-10 is ineffective in suppressing the cell growth. In contrast, liposomally formulated A-10 suppressed cell growth and has an $IC_{50}$ near 30 μM. Although the part of enhanced antineoplastic effect seen in this early study can be attributed to excessive levels of lipid (drug:lipid ratio=1:30) it is clear that the liposomal formulation of A-10 has an even higher level of antineoplastic activity. Work with several other lines indicate that the $IC_{50}$ for the components of A-10 is between 20 and 25 mM. By extension this suggests that the liposomal formulation of A-10 is more than 700 times more effective than non-liposomal A-10.

EXAMPLE 9

Antineoplastic Effects Free and Liposomal AS2-1, PG and PN

The impact of liposomal formulations on the antineoplastic activity of AS2-1 or PG or PN was examined in human glioblastoma (U87) cells. Experiments with this cell line plated 3000 cells per well and following a four day interval to allow the cells to enter the exponential growth phase the test agents were added. The media was replaced on day three and cell counts were obtained at day 3 and 7. Levels of liposomes are equivalent across the levels of the test agent.

Figure 13:
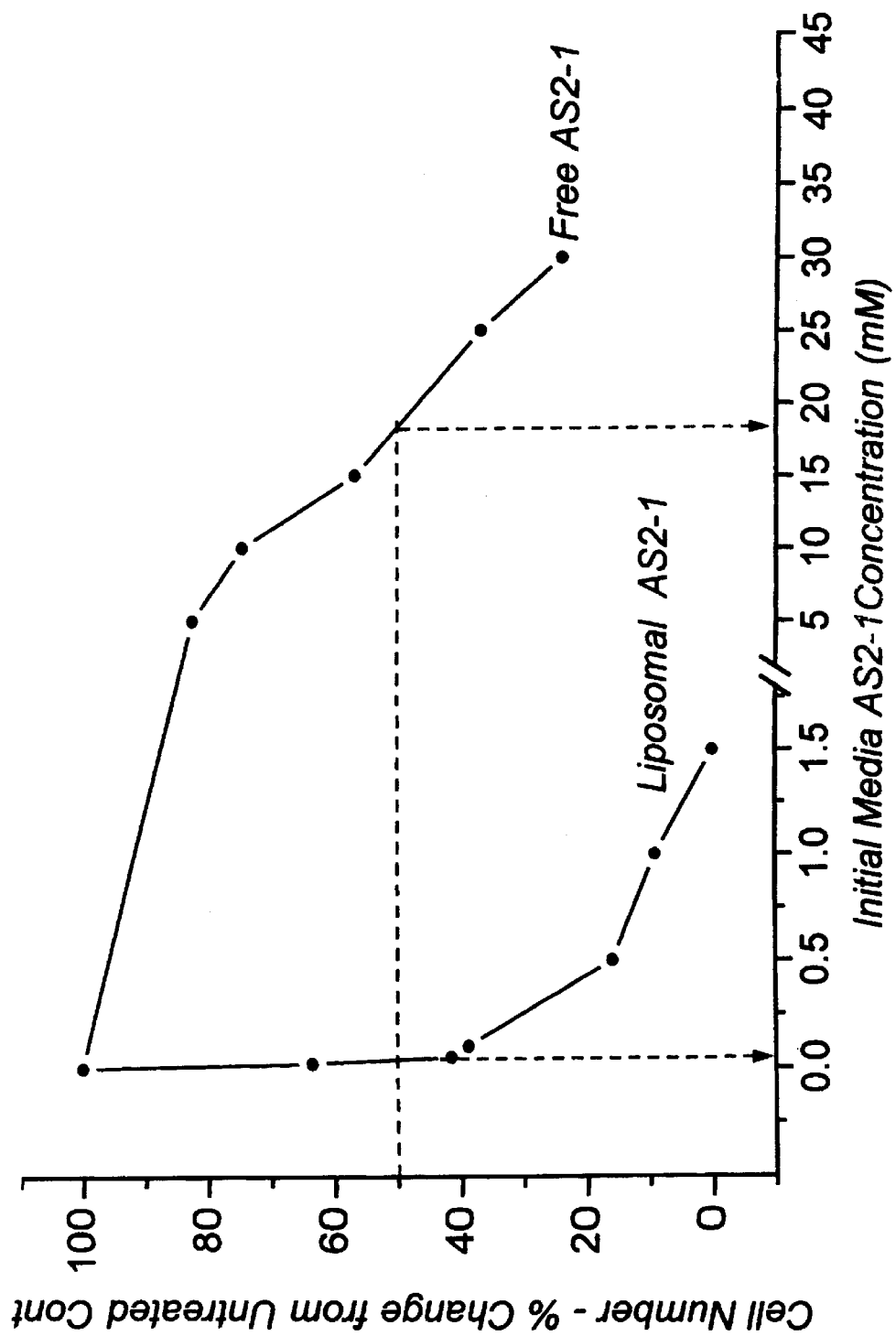
FIG. 13 shows the concentration dependence of cell numbers following treatment with free or liposomal AS2-1.

FIG. 13 shows that the antineoplastic activity of AS2-1 against U87 human glioblastoma cells is increased 900 fold by liposomal formulations.

Figure 14:
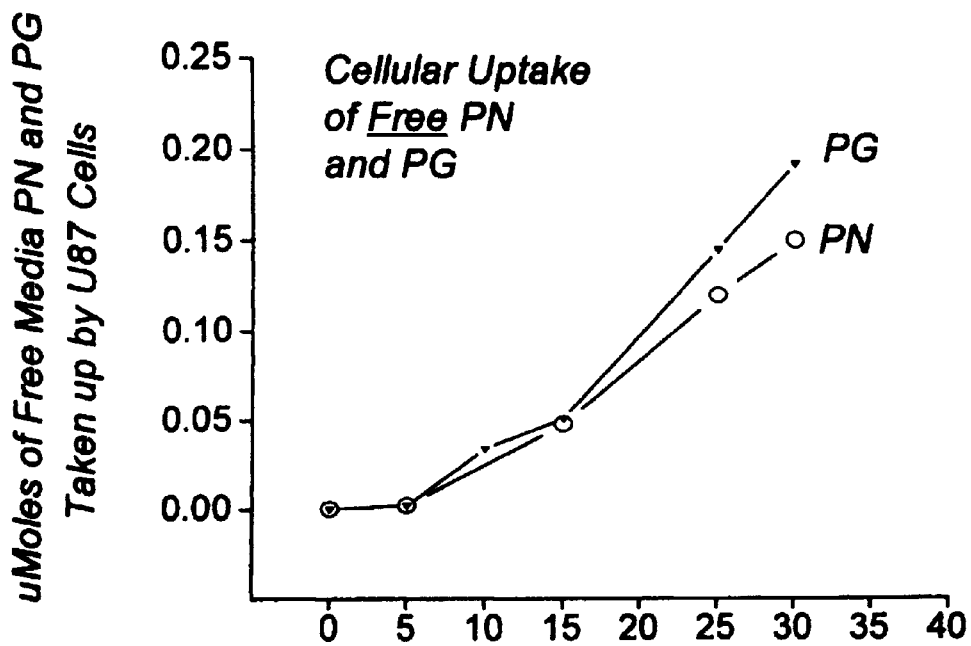
FIG. 14 shows the cellular uptake of free PN and PG.
Figure 15:
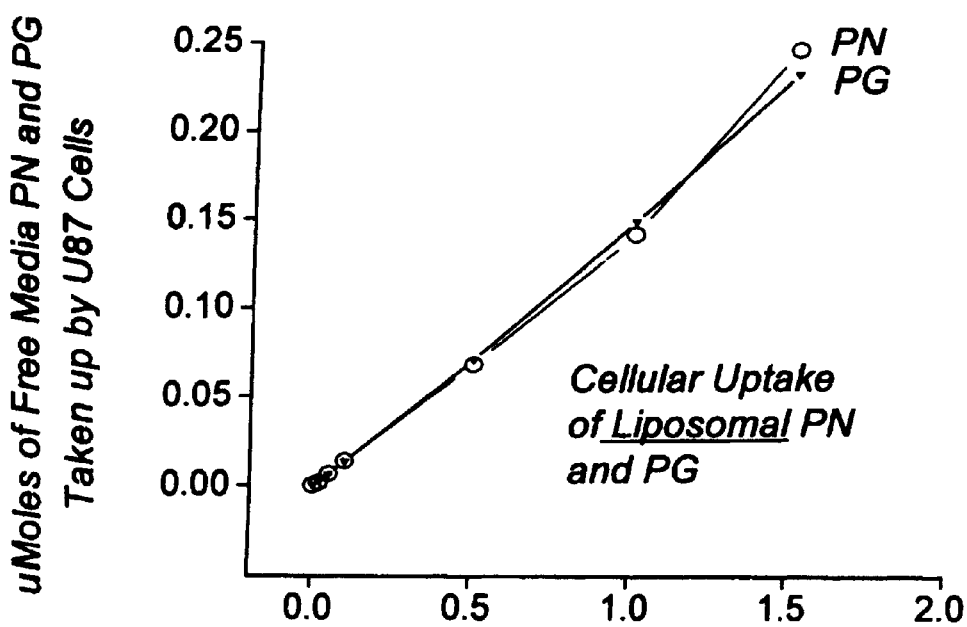
FIG. 15 shows the cellular uptake of liposomal PN and PG.
Figure 16:
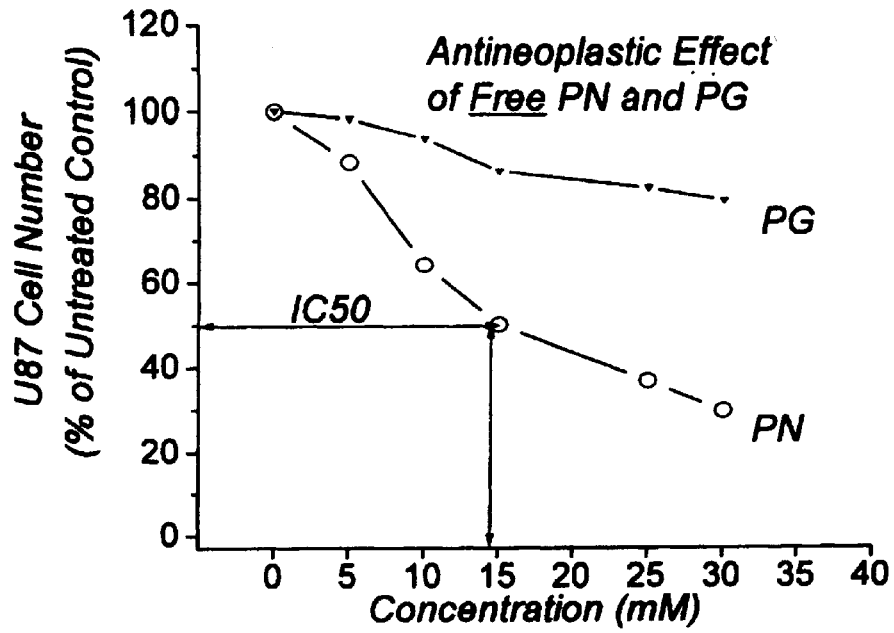
FIG. 16 shows the antineoplastic effect of free PN and PG.
Figure 17:
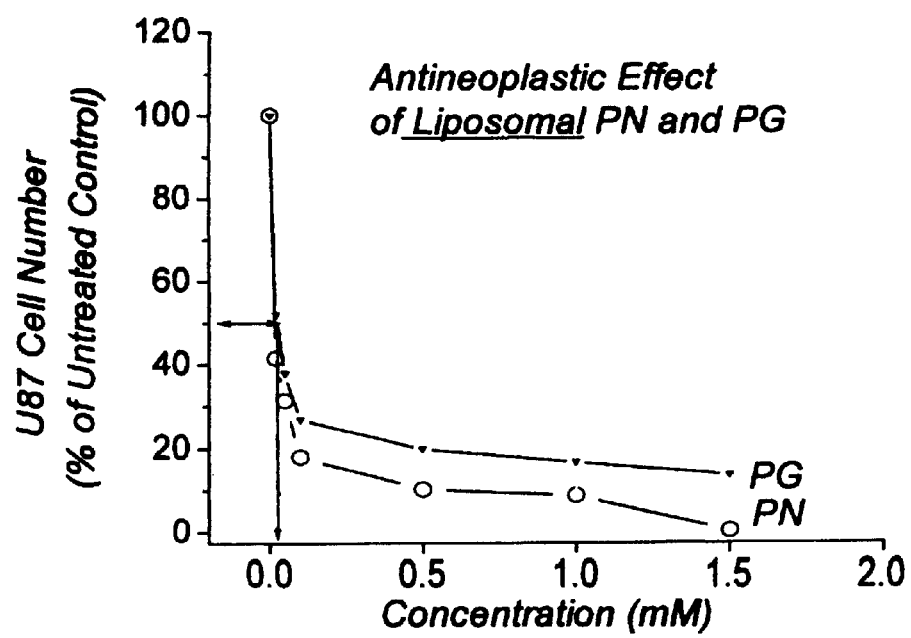
FIG. 17 shows the antineoplastic effect of liposomal PN and PG.

FIGS. 14 and 15 show the cellular uptake of free and liposomal phenylacetate (PN) and phenylactylgiutamine (PG), while FIGS. 16 and 17 show the antineoplastic activity of free and liposomal phenylacetate (PN) and phenylactylglutamine (PG). These compounds are the major components of antineoplaston AS2-1 and A-10 therapies, respectively. The data shown in FIG. 13 are from a three day incubation but similar data was observed after a 7 day incubation with media change on day 3. It can be seen that during this 3 day interval the uptake of free PN and PG is equivalent and is concentration dependent. Expressed on a per cell basis the uptake of 30 mM free PN by the U87 cells is 50 pmoles. This value approximates the ~55 pmole value found for BT-20 cells (see FIGS. 3, 4 and 5).

FIG. 16 shows the antineoplastic activity of free PN and PG on the U87 cell. It can be seen that the three day $IC_{50}$ for PN is near 15 mM ($IC_{50}$=the concentration producing a half maximal antineoplastic effect). In contrast, the antineoplastic activity of PG is much weaker and fails to produce an $IC_{50}$. It is interesting that although PG has an uptake pattern virtually identical to PN it has, in this cell line, a much weaker antineoplastic effect. This indicates that the level of uptake per se is not predictive of antineoplastic activity.

FIG. 17 shows the antineoplastic effect of liposomal PN and PG. It can be seen that antineoplastic activity is markedly enhanced in liposomal formulations. The $IC_{50}$ for liposomal PN and PG are similar and are near 0.02 mM. The $IC_{50}$ for liposomal PN is 750 times lower than that of free PN. While the enhancement of PG antineoplastic activity in this cell line is undetermined, from the above observations that the $IC_{50}$ for PG is greater than 30 mM, it follows that the activity must be increased substantially more than 750 fold.

FIG. 15 shows the uptake of liposomally formulated PN and PG. As was the case with the free form of these antineoplastons, the levels of cellular uptake for liposomal formulated PN and PG are similar. Another similarity between free and liposomally formulated PN and PG is that uptake is concentration dependent. It is obvious from a comparison of FIGS. 11 and 12 that although free and liposomal antineoplaston agents produce equivalent levels of cellular uptake the concentrations of free forms required to produce this effect are 20 times higher than that of the liposomal formulation. Likewise, in situations where free and liposomal PN produce similar levels antineoplastic activity (e.g., the $IC_{50}$) the levels of uptake for liposomal formulations are lower by a factor of 30 (liposomal PG total uptake at the $IC_{50}$ value of 0.02 mM=0.00147 u moles: free PG total uptake at the $IC_{50}$ value of 15 mM=0.048 uM).

Although the weak antineoplastic activity of free PG in this cell line prevented the $IC_{50}$ from being precisely determined, it seems clear that this value is well above 30 mM (see FIG. 10 lower left panel). This suggests that the absolute uptake of liposomal PG (0.00227 $\mu$moles at the $IC_{50}$ of 0.02 mM) is at least 80 times lower the 0.192 $\mu$moles observed with 30 mM free PG.

The work presented here demonstrates that the antineoplastic activity and cellular uptake of antineoplastons is markedly enhanced by formulating these compounds in liposomes. Liposomal formulations were also found to alter the intracellular metabolic fate of antineoplastons. The observation that liposomal PN and PG have an enhanced antineoplastic activity with lower levels of cellular uptake indicates that the increased activity is not the simple result of enhanced uptake. Instead the liposomal formulation result in an intracellular targeting of antineoplastons to intracellular sites that regulate cell viability and proliferation.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A pharmaceutical composition comprising lipids in a liposomal formulation and an antineoplaston agent within the liposomal formulation, wherein the antineoplaston agent comprises 3-phenylacetylamino-2,6, piperidinedione wherein the molar ratio of antineoplaston agent to lipid is between 1:0.1 to 1:100.

2. A pharmaceutical composition comprising lipids in a liposomal formulation and an antineoplaston agent within the liposomal formulation, wherein the antineoplaston agent comprises phenylacetate and phenylacetylglutamine wherein the molar ratio of antineoplaston agent to lipid is between 1:0.1 to 1:100.

3. The pharmaceutical composition according to claim 2, wherein the phenylacetylglutamine is L-phenylacetylglutamine.

4. The pharmaceutical composition according to claim 2, wherein the molar ratio of phenylacetate to phenylacetylglutamine is 8 to 1.

5. A pharmaceutical composition comprising lipids in a liposomal formulation and an antineoplaston agent within the liposomal formulation, wherein the antineoplaston agent comprises phenylacetylglutamine and isophenylacetylglutamine wherein the molar ratio of antineoplaston agent to lipid is between 1:0.1 to 1:100.

6. The pharmaceutical composition according to claim 5, wherein the molar ratio of phenylacetylglutamine to isophenylacetylglutamine is 4 to 1.

7. A method of treating malignant neoplastic disease, comprising administering to the patient a pharmaceutical composition according to any one of claims 3 to 8.

* * * * *

UNITED STATES PATENT AND TRADEMARK OFFICE
CERTIFICATE OF CORRECTION

PATENT NO.   :   6,013,278
DATED        :   January 11, 2000
INVENTOR(S)  :   Byra et al.

It is certified that error appears in the above-identified patent and that said Letters Patent is hereby corrected as shown below:

Claim 5, column 12, line 44, delete "isophenylacetylglutamine" and replace with --iso–phenylacetylglutamine--.

Claim 7, column 12, line 52, delete "claims 3 to 8" and replace with --claims 1 to 6--.

Signed and Sealed this

Nineteenth Day of September, 2000

Attest:

Q. TODD DICKINSON

Attesting Officer

Director of Patents and Trademarks